United States Patent [19]
Horiuchi et al.

[11] Patent Number: 4,880,416
[45] Date of Patent: Nov. 14, 1989

[54] DERMAL BANDAGE AND DERMAL PREPARATION

[75] Inventors: Tetsuo Horiuchi; Yuichi Inoue, both of Osaka, Japan

[73] Assignee: Nitto Electric Industrial Co., Ltd., Osaka, Japan

[21] Appl. No.: 266,318

[22] Filed: Oct. 31, 1988

Related U.S. Application Data

[63] Continuation of Ser. No. 929,115, Nov. 10, 1986, abandoned.

[30] Foreign Application Priority Data

Nov. 8, 1985 [JP] Japan .................................. 60-251734
Sep. 9, 1986 [JP] Japan .................................. 61-212970

[51] Int. Cl.⁴ .............................................. A61F 13/02
[52] U.S. Cl. ..................................... 604/307; 128/155; 128/156; 604/304; 424/427; 424/445
[58] Field of Search ................. 128/156, 640; 604/304, 604/307; 424/427, 445

[56] References Cited

U.S. PATENT DOCUMENTS

| | | | |
|---|---|---|---|
| 4,307,717 | 12/1981 | Hymes et al. | 604/307 |
| 4,367,732 | 1/1983 | Pousen et al. | 604/307 |
| 4,485,809 | 12/1984 | Dellas | 604/307 |
| 4,588,580 | 5/1986 | Gale et al. | 604/307 |
| 4,643,180 | 2/1987 | Feld et al. | 604/307 |
| 4,644,792 | 10/1987 | Nick et al. | 604/307 |
| 4,655,768 | 4/1987 | Morecki et al. | 604/307 |
| 4,675,009 | 6/1987 | Hymes et al. | 604/304 |
| 4,685,455 | 8/1987 | Vrouenroets | 604/307 |
| 4,699,146 | 10/1987 | Sieverding | 128/640 |

FOREIGN PATENT DOCUMENTS

| | | |
|---|---|---|
| 200508 | 11/1986 | European Pat. Off. |
| 86308699 | 7/1988 | European Pat. Off. |
| 2086224 | 5/1982 | United Kingdom |

OTHER PUBLICATIONS

Chemical Abstracts, vol. 102, No. 6, 11th Feb. 1985, p. 328, abstract No. 50945g, Columbus, Ohio; U.S. Patent Abstracts of Japan, vol. 9, No. 45 (C-268) [1768] 26th Feb. 1985 (relating to JP 59-186913).

Primary Examiner—Richard J. Apley
Assistant Examiner—N. Paul
Attorney, Agent, or Firm—Sughrue, Mion, Zinn, Macpeak & Seas

[57] ABSTRACT

A dermal bandage comprising a film-like adhesive material comprising at least one of polycarboxylic acids and polycarboxylic acid anhydrides, and a vinyl acetate polymer, and a dermal preparation comprising a film-like adhesive material containing drug, comprising at least one of polycarboxylic acids and polycarboxylic acid anhydride, and a vinyl acetate polymer are disclosed. The dermal bandage and dermal preparation exhibit strong adhesion of long duration only upon water absorption and is useful for prevention of running off of drugs applied to the skin or protection of affected parts of the skin.

24 Claims, 3 Drawing Sheets

DERMAL BANDAGE AND DERMAL PREPARATION

This is a continuation of application Ser. No. 969,115 filed Nov. 10, 1987, now abandoned.

FIELD OF THE INVENTION

This invention relates to a dermal bandage which is useful for prevention of falling off of dermally applied ointments, creams, solutions, powders, etc., or protection of affected parts of the skin, and a dermal preparation comprising such a bandage having incorporated therein a drug.

BACKGROUND OF THE INVENTION

Conventional dermal bandages include various types of adhesive plasters, adhesive tapes containing a drug for precutaneous administration, and the like. Wounds may be treated by applying gauze or absorptive cotton with, if necessary, a drug on the damaged part, and fixing it with adhesive tape. Further, a liquid bandage comprising a solution of polymeric material is also available, which is applied to the affected part with a spray or a brush, followed by removing the solvent by vaporization to provide a protective film on the affected part.

However, the treatment with gauze or absorptive cotton has a problem that the gauze or absorptive cotton adheres to the wound and, when removed, redamages the wound under recovery. The liquid bandage frequency causes pain upon application to the damaged skin due to the organic solvent used for dissolving the protective film-forming polymeric material. Moreover, it encounters a safety problem due to skin penetration of the organic solvent through the wound. Since cataplasms are composed of a paste of a water-soluble polymer with water and non-woven cloth or flannel as a support, they are not so irritative on the skin. However, they exhibit poor adhesion to the skin to give a feel foreign to the skin. The plasters or drug-containing adhesive tapes comprise a natural or synthetic rubber adhesive material containing a drug for percutaneous administration have recently been increasing in kind, but their direct use on the damaged skin has problems in that they not only exhibit strong adhesion but cause excessive maceration or dermatitis on the skin. In addition, since the adhesive tapes or the like should be applied to the dry skin as a prerequisite to their effect, they are hardly adhered to the skin wet with solutions, ointments, etc.

Therefore, it has long been demanded to develop dermal bandages which can satisfactorily be adhered to the damaged skin either directly or via drugs.

Water-soluble polymeric materials, such as polycarboxylic acids and anhydrides thereof, exhibit per se shape retention properties. They exhibit strong adhesion on absorbing a small amount of water, but absorption of excess water causes a reduction in viscosity and degradation to make a substantially dissolved state, thus resulting in loss of adhesiveness.

The inventors have extensively conducted a series of investigations in an attempt of improve the adhesion behavior of these water-soluble polymeric materials, i.e., loss of adhesion upon excessive water absorption, while retaining the strong adhesion observed when an appropriate amount of water is absorbed. To this effect, studies were directed to water-insolubilization of these water-soluble polymers. As a result, it has now been found that polycarboxylic acids or anhydrides thereof and vinyl acetate polymers have appropriate compatibility with each other and, when they are maintained in a compatible state or a nearly compatible state, substantial water-insolubilization of the polycarboxylic acids or anhydrides thereof can be achieved with their strong adhesiveness being retained or rather enhanced. It has been noted, therefore, that thin and soft films obtained from the compatible mixture of these two components do not undergo degradation due to water absorption in a wet state but exhibit long-lasting strong adhesion. The present invention has been completed based on this finding.

SUMMARY OF THE INVENTION

Accordingly, one object of the present invention is to provide a dermal bandage which can be strongly adhered to the skin even when it is wet, can be adhered directly to the damaged skin without causing irritation on the skin, has excellent adhesiveness, and softness, and gives no feel of foreign matter.

Another object of the present invention is to provide a dermal preparation comprising such a dermal bandage having incorporated therein a drug.

The dermal bandage according to the present invention comprises a film-like adhesive material or a composite of the film-like adhesive material and a soft backing member, the film-like adhesive material comprising at least one of a polycarboxylic acid and a polycarboxylic acid anhydride, and a vinyl acetate polymer.

The dermal preparation according to the present invention comprises a film-like adhesive material containing a drug or a composite of the film-like adhesive material containing a drug and a soft backing member, the film-like adhesive material comprising at least one of a polycarboxylic acid and a polycarboxylic acid anhydride, and a vinyl acetate copolymer.

DETAILED DESCRIPTION OF THE INVENTION

The dermal bandage according to the present invention can be prepared by, for example, dissolving at least one of a polycarboxylic acid and a polycarboxylic acid anhydride, and a vinyl acetate polymer in a common solvent and flow-casting the solution, followed by drying to form a film. This process easily produces a very thin film.

The dermal preparation according to the present invention can be prepared by, for example, dissolving at least one of a polycarboxylic acid and a polycarboxylic acid anhydride, and a vinyl acetate polymer in a common solvent, adding a drug to the solution, followed by mixing, and rapidly flow-casting the solution, followed by drying to form a film. This process also easily produces a very thin film.

The dermal preparation according to the present invention can be further prepared by dissolving at least one of a polycarboxylic acid and a polycarboxylic acid anhydride, and a vinyl acetate polymer in a common solvent, rapidly flow-casting the solution, followed by drying to form a film, and dipping the film in a solution of drug or coating the surface of the film with a solution of drug, followed by drying to form a film containing a drug.

Examples of the polycarboxylic acids which can be used in the present invention includes the acrylic acid polymers, the methacrylic acid polymers, and combinations thereof. Specific examples of the acrylic acid polymers include an acrylic homopolymer and copolymers of acrylic acid and acrylic esters, e.g., butyl acrylate, 2-ethylhexylacrylate, etc., methacrylic esters, e.g., methyl methacrylate, etc., or vinyl monomers, e.g., vinyl acetate, etc., and copolymers, e.g., a carboxylvinyl polymer. Specific examples of the methacrylic acid polymer include a methacrylic acid homopolymer and a copolymer of methacrylic acid with the same comonomers as enumerated for the acrylic polymers.

Examples of the polycarboxylic acid anhydride which can be used in the present invention include a maleic anhydride homopolymer, a maleic anhydride-methyl vinyl ether copolymer, and the like.

Better results can be obtained when the polycarboxylic acid acid anhydride contains 20% by weight or more of a —COOH group and the polycarboxylic acid anhydride contains 16% by weight or more of a CO—O—CO-group.

The amount of at least one of polycarboxylic acid and polycarboxylic acid anhydride in the film-like adhesive material is preferably 20 to 75% by weight based on the weight of the film-like adhesive material.

Examples of the vinyl acetate polymer which can be used in the present invention include not only a vinyl acetate homopolymer but copolymers of vinyl acetate and vinyl monomers, e.g., acrylic esters, and a partially saponified product of a vinyl acetate homopolymer. These vinyl acetate polymers can be used either individually or in combination of two or more thereof.

The vinyl acetate polymers to be used preferably have an average molecular weight (viscosity average molecular weight) of 60,000 or more. If the average molecular weight is less than 60,000, the resulting adhesive film has a poor water resistance, failing to achieve the desired effects.

Solvents common to at least one of the above-described polycarboxylic acid and polycarboxylic acid anhydride (hereinafter referred to as "polycarboxylic acids") and the vinyl acetate polymer include (1) lower alcohols, e.g., methanol, ethanol, etc., (2) mixed solvents comprising (1) as a major component and organic solvents soluble therein, e.g., acetone, ethyl acetate, etc., and (3) mixed solvents comprising (1) or (2) and water. The content of the organic solvents in the mixed solvents (2) is preferably limited to 30% by weight or less since contents more than 30% by weight make it difficult to dissolve polycarboxylic acids. The water content in the mixed solvents (3) is preferably limited to 30% by weight or less. If it exceeds 30% by weight, dissolution of the vinyl acetate polymers tends to become difficult.

In the preparation of the film-like adhesive material in the dermal bandage or dermal preparation according to the present invention, it is preferred to select the mixing ratio of polycarboxylic acids and the vinyl acetate polymer so that value A as defined below may fall within the range of from 15 to 55.

$$A = \frac{\text{Weight of —COOH in Film-like Adhesive Material} + \frac{5}{4} \text{Weight of —CO—O—CO— in Film-like Adhesive Material}}{(\text{Weight of Polycarboxylic Acids} + \text{Weight of Vinyl Acetate Polymer}) \text{ in Film-like Adhesive Material}} \times 100$$

As the value A becomes greater, the adhesive strength of the film-like material to the skin tends to increase, but the duration of adhesion tends to decrease. On the other hand, as the value A becomes smaller, there is an observable tendency to decrease the adhesive strength but increase the duration of adhesion. If value A is less than 15, it is difficult to obtain a sufficient adhesion. If it exceeds 55, insufficient duration of adhesion results. For this reason, the mixing ratio of the polycarboxylic acids and the vinyl acetate polymer is preferably controlled so as to be in the range of from 15 to 55. More specifically, in the case where polyacrylic acid is used as the polycarboxylic acid, value A could fall within the above range to obtain favorable results by controlling the proportion of polyacrylic acid in film-like adhesive material to a range of from 24% to 72% by weight.

Care should be taken to sufficiently dissolve the polycarboxylic acids and the vinyl acetate polymer in a common solvent. Concentrations of these polymeric materials in the resulting solution are not particularly restricted, but are preferably adjusted not to exceed 40% by weight because too a high concentration of the polymeric materials, i.e., too a high viscosity of the polymer solution, tends to result in difficulty of film casting.

Film casting of the solution of polycarboxylic acids and vinyl acetate polymer can be carried out by casting the solution on an appropriate release film, such as polyethylene-laminated paper, and rapidly drying in a high-temperature air bath, such as a drying oven or a drying tower. Adequate time and temperature for drying are preferably from 60° to 120° C. in temperature and from about 1 to about 20 minutes in time, though varying depending on the composition of the common solvent used, the solid content in the solution, the casting thickness, and the like.

The very thin film-like adhesive material thus obtained can be used as it is as the dermal bandage or dermal preparation according to the present invention. The thickness of the film-like adhesive material can be controlled by varying the casting amount and the like and preferably fall within the range of from 5 to 500 μm. It the thickness is less than 5 μm, it is difficult to obtain sufficient adhesion properties. A thickness exceeding 500 μm causes a feel foreign to the skin and gives a tendency to impair the softness of the film-like material.

The thus prepared soft film-like adhesive material according to the present invention shows no adhesion in a dry state but exerts firm adhesion to the skin upon water absorption. Even when the film-like adhesive material is immersed in water, it swells almost uniformly, with little elution of the polycarboxylic acid component, which indicates substantial water-insolubilization of the polycarboxylic acid component. The above-described adhesion behavior in a dry or wet state as well as the property to retain the film form with adhesiveness even when immersed in water are epoch-making characteristics.

If desired, it is possible to make a water-free dry film-like adhesive material of the invention well adhesive to the skin by incorporating an appropriate amount of a plasticizer, e.g., polyethylene glycol, in the film-like adhesive material.

The above-described excellent characteristics of the film-like adhesive material according to the present invention can first be obtained by using both the polycarboxylic acids and the vinyl acetate polymer. Individual use of either one of these components does not reach such an achievement.

The drug which can be contained in the film-like adhesive material according to the present invention can be solid or liquid at room temperature so long as the drug is percutaneously absorbed when the dermal preparation is adhered to the skin, and is dissolved or dispersed in the film-like adhesive material.

Examples of the drug are exemplified below.

(i) Corticosteroids: hydrocortisone, predonisolone, beclomethasone propionate, flumethasone, triamcinolone, triamcinolone acetonide, fluocinolone, fluocinolone acetonide, fluocinolone acetonide acetate, clobetasol propionate, etc.

(ii) Analgesic anti-inflammatory agents: acetaminophen, mefenamic acid, flufenamic acid, indomethacin, diclofenac, diclofenac sodium alclofenac, oxyphenbutazone, phenylbutazone, ibuprofene, flurbiprofen, salicylic acid, lmenthol, camphor, sulindac, tolmetin sodium, naproxen, fenbufen, etc.

(iii) Hypnotic sedatives: phenobarbital, amobarbital, cyclobarbital, triazolam, nitrazepam, lorazepam, holoperidol, etc.

(iv) Tranquilizers: fluphenazine, thioridazine, lorazepam, flunitrazepam, chlorpromazine, etc.

(v) Antihypertensives: clonidine, clonidine hydrochloride, pindolol, propranolol, propranolol hydrochloride, bupranolol, indenolol, nipadipine, lofexidine, nitrendipine, nipradilol, bucumolol, nifedipine, etc.

(vi) Antihypertensive diuretics: hydrothiazide, bendrofluméthiazide, cyclopenthiazide, etc.

(vii) Antibiotics: penicillin, tetracycline, oxytetracycline, fradiomycin sulfate, erythromycin, chloramphenicol, etc.

(viii) Anesthetics: lidocaine, dibucaine hydrochloride, benzocaine, ethyl aminobenzoate, etc.

(ix) Antimicrobial agents: benzalkonium chloride, nitrofurazone, nystatin, acetosulfamine, clotrimazole, etc.

(x) Antifungal agents: pentamycin, amphotericin B, pyrrolnitrin, clotrimazole, etc.

(xi) Vitamins: vitamin A, ergocalciferol, cholecalciferol, octotiamine, riboflavine butyrate, etc.

(xii) Antiepileptics: nitrazepam, meprobamate, clonazepam, etc.

(xiii) Coronary vasodilators: nitroglycerin, dipyridamole, isosorbide dinitrate, erythritol tetranitrate, pentaerythritol tetranitrate, propatyl nitrate, etc.

(xiv) Antihystaminic agents: diphenhydramine hydrochloride, chlorpheniramine, diphenylimidazole, etc.

(xv) Antitussives: dertromethorphan (hydrobromide), terbutoline (sulfate), ephedrine (hydrochloride), salbutanol (sulfate), isoproterenol (sulfate, hydrochloride), etc.

(xvi) Sexal hormones: progesterene, estradiol, etc.

(xvii) Thymoleptics: doxepin, etc.

(xviii) Ameliorants of cerebral circulation: hydergine, ergot alkaloids, ifenprodil, etc.

(xiv) Antiemetic agents, Antiulcer agents: metoclopramide, clebopride, domperidone, scopolamine, 5-fluoro uracil, scopolamine hydrobromide, mercaptopurine, etc.

(xx) Bioactive agent: polypeptides, e.g., TRH, LHRH, etc., prostaglandines, etc.

(xxi) Other drugs: fentanyl, digoxin, desmopressin, dihydroergotamine methane sulfonate, dihydroergotamine tartrate, etc.

Those drugs can be used in combination of two or more, if desired and necessary.

Although varying depending on the kind of drugs, the amount of drug is 0.001 to 30% by weight, preferably 0.05 to 20% by weight, based on the weight of the film-like adhesive material, taking into consideration the pharmacologicol effect and adhesion involved.

The film-like adhesive material according to the present invention can be used alone as the dermal bandage or the dermal preparation when containing the drug. However, the film-like adhesive material can be combined with a soft backing member to form a composite product.

The preparation of the composite product is explained below by reference to the dermal bandage, but the same manner can be applied to the composite product of the dermal preparation.

The composite product can be produced by laminating the film-like adhesive material according to the present invention on a soft backing member in a conventional manner, such as hot pressing, bonding with adhesives, and the like. The preparation of the film-like adhesive material and the lamination thereof on the backing member may be conducted simultaneously by flow casting the film-forming compound on the soft backing member. The latter simultaneous process is advantageous in that hot pressing or application of an adhesive is unnecessary, thereby to simplifying the production.

The backing member which can be used in the composite product of the present invention includes plastic films of polyethylene, vinyl acetate resins, ethylene-vinyl acetate copolymers, polyvinyl chloride, polyurethane, etc., metal foils, e.g., aluminum foil, tin foil, etc., non-woven fabric, cloth, and laminate films composed of cloth or paper and a plastic film. From the standpoint of safety and feel of touch, the preferred backing members are plastic films, such as polyethylene, vinyl acetate resins, ethylene-vinyl acetate copolymers, etc. The backing member preferably has a thickness of from 5 to 1,000 $\mu$m in view of handling properties and the feel of touch on use. The total thickness of the film-like adhesive material and the backing member preferably ranges from 30 to 1,500 $\mu$m. Composite products having total thickness less than 30 $\mu$m have poor handling properties. A total thickness exceeding 1,500 $\mu$m is likely to cause a feel foreign to the skin upon use.

In the case that a plasticizer is not added, the dermal bandage or dermal preparation according to the present invention can be brought into the market as a soft film-like adhesive material which exhibits adhesion only upon absorption of water while showing no adhesion in a dry state (hereinafter referred to as "water-free type"). When it is intended to apply the film-like adhesive material to unwet sites, a part or the whole of the water-free type dermal bandage or dermal preparation may be moistened by spraying water or an alcohol for disinfection, or production conditions may be selected so that moisture may remain in the resulting product. Such a product can be put into the market as a "water-containing type" which strongly adheres to the skin simply by pressing. In this case, a desired adhesive strength can be obtained by controlling the water content. The water content control is effected through, for example, appropriate selection of drying conditions or adjustment of the amount of water to be used for spraying or dipping. Further, the water-free type can be rendered adhesive by incorporating a plasticizer, e.g., polyethylene glycol, into the film-forming compound. If any plasticizer is not particularly incorporated, the film-like adhesive material of the present invention rapidly exerts adhesiveness to the damaged or wet skin that is less subject to adhesion due to sweat or moisture on the skin, drugs applied, bleeding, and the like. By the aid of the film-like adhesive material of the present invention, loss of drugs due to running off can be prevented while giving protection to the skin to thereby ensure percutaneous absorption of the drug and accelerated healing of the damaged skin. The present invention is also characterized in that such an adhesion state lasts prolonged periods of time.

For the purpose of ensuring moisture retention and adhesion, the film-like adhesive material according to the present invention can further contain a polyhydric alcohol, e.g., glycerin, sorbitol, ethylene glycol, diethylene glycol, tirethylene glycol, polyethylene glycol, propylene glycol, polypropylene glycol, mannitol, polyoxyethylenepolyoxypropylene glycol, etc.

As described above, the dermal bandage and dermal preparation according to the present invention have two embodiments, i.e., a water-containing type and a water-free type, and their characteristics, such as adhesion, are influenced by the water content or the compounding ratio of the above-described polyhydric alcohol. In this connection. the total content of water and the polyhydric alcohol is preferably up to 200% by weight based on the total amount of the polycarboxylic acids and the vinyl acetate polymers, with the water content being up to 50% by weight based on the whole compound. If the content of water or a polyhydric alcohol exceeds the above upper limit, there is a fear of insufficiency in any of adhesion, cohesive force, film strength, and the like. Here, the cohesive force can be controlled by irradiation.

In order to avoid irritation on the damaged skin or to weaken influences upon drugs, if applied, such as induction of chemical reactions or decomposition of the drugs, the film-like adhesive material of the present invention can further contain salts or bases capable of neutralizing the polycarboxylic acids. Examples of the salts or bases include salts of metals and weak acids (e.g., salts of sodium, potassium, calcium, magnesium or the like and carboxylic acids such as acetic acid, lactic acid or citric acid), oxides of metals (e.g., zinc oxide, calcium oxide, magnesium oxide or the like), hydroxides of metals (e.g., sodium hydroxide, potassium hydroxide, calcium hydroxide, magnesium hydroxide or the like), and various amines (e.g., triethanol amine, diisopropanol amine or the like).

The amount of the neutralizing agent to be added is preferably from 0.2 to 1.3 equivalents based on the polycarboxylic acid, although greatly varying depending on its kind. With an insufficient degree of neutralization, irritation on the damaged skin may not be alleviated. An excessive degree of neutralization sometimes deteriorates resistance to water or perspiration.

If desired, the film-like adhesive material in the dermal bandage or dermal preparation according to the present invention may contain other additives, such as colorants, flavors, softeners, etc., so far as the addition does not impair adhesion properties of the film-like adhesive material. For example, when both the film-like adhesive material and the backing member are colorless, addition of a colorant to either one of them makes it easy to distinguish between the surface side and the back side.

As described above, the dermal bandage and dermal preparation according to the present invention comprise a soft and thin film-like adhesive material prepared from a mixture of at least one of a polycarboxylic acid and a vinyl acetate polymer with or without a backing member. Both the film-like adhesive material and the film-like adhesive material on the backing member perfectly and easily fit any part of the body due to their softness and strong adhesion. Moreover, the adhesion exerted is maintained for an extended peiod of time. Peel tests using a collagen film swollen with water as an adherend (peel angle: 180°) revealed that the adhesiveness was from about 20 to about 200 g/2.5 cm width, as shown in the Examples hereinafter given. These results indicate remarkable effects on prevention of running off of administered drugs or protection of the damaged skin.

In particular, since the polycarboxylic acids which constitute the film-like adhesive material are substantially insolubilized, the dermal bandage or dermal preparation, even when immersed in water, is only swollen with water while retaining high water-resistance without undergoing degradation due to water absorption.

This invention will now be illustrated in greater detail by reference to the following Examples, but it should be understood that they are not intended to limit the present invention. In these examples, all the parts, percents and ratios are by weight unless otherwise indicated.

EXAMPLE 1

Five parts of a carboxyvinyl polymer (CVP) and 5 parts of a vinyl acetate resin (PVAc) (degree of polymerization: about 1,500) were dissolved in 90 parts of methanol, which is a solvent common to them, to form a uniform solution. The solution was last on a paper separator, dried, and peeled off to obtain a film-like adhesive material having a thickness of 30 μm. Value A of the resulting film-like adhesive material calculated was 31.3.

The film-like adhesive material was then hotpressed onto a 40 μmthick polyethylene film with an aluminum deposit to prepare a dermal bandage. The resulting product was evaluated for performances through an adhesion test and peel test in accordance with the following test methods. The results obtained are shown in Table 1.

Adhesion Test Method:

A circular specimen of 10 mm in diameter was cut out of the sample, adhered to a water-swollen crosslinked collagen film fixed to a phenol resin plate, and immersed in water at 37° C. The state of the sample in water was observed.

Peel Test Method:

The sample was cut into a strip of 2.5 cm in width and 15 cm in length. The specimen was adhered to a water-swollen crosslinked collagen film and immersed in water in the same manner as described above. After immersion for a prescribed period of time, the peel strength at a peel angle of 180° C. was determined by means of a Schopper type tensile strength tester.

TABLE 1

| Adhesion | Peel Strength (g/2.5 cm-width) | | | | |
|---|---|---|---|---|---|
| | 10 min | 30 min | 60 min | 120 min | 240 min |
| A slight swelling observed in the peripheral portion with no other change. Strong adhesion maintained after 5 hours' immersion. | 110 | 105 | 95 | 85 | 90 |

EXAMPLES 2 TO 6

A 10% methanol solution of CVP and a 10% methanol solution of PVAc (degree of polymerization: about 2,500) were mixed at varying proportions as shown in Table 2. The mixed solution was cast on a paper separator, dried, and peeled off to prepare a film-like adhesive material having a thickness of 20 μm. The film was hot pressed onto a 50 μm thick polyvinyl acetate film (degree of polymerization: about 2,500) to obtain a dermal bandage.

Each of the resulting samples was evaluated in the same manner as in Example 1, except that the time of immersion in water for the peel test was fixed at 10 minutes. The results obtained are shown in Table 2 below. In Table 2, the adhesion observed in the adhesion test was expressed in terms of time period for which the adhesion was retained.

TABLE 2

| | Example No. | | | | |
|---|---|---|---|---|---|
| | 2 | 3 | 4 | 5 | 6 |
| Mixing Ratio (CVP:PVAc) | 2:8 | 3:7 | 5:5 | 7:3 | 8:2 |
| Value A | 12.5 | 18.8 | 31.3 | 43.8 | 50.0 |
| Adhesion Time (hr) | 8< | 8< | 8< | 3.2 | 1.5 |
| Peel Strength (g/2.5 cm width) | 20 | 60 | 110 | 160 | 200 |

It can be seen from Table 2 that the film-like adhesive materials of Examples 3 to 5, in which value A falls within the range of from 15 to 55, satisfy both requirements of strength and duration of adhesion. Further, the sample of Example 6 having value A of 50, which falls within the range of 15 to 55, shows a relatively short adhesion time, but has sufficient strength. Therefore, it is possible to use this sample depending on the specific purpose of use, e.g., when a short adhesion time is required. On the other hand, the sample of Example 2, in which the CVP:PVAc ratio is 2:8 and value A is less than 15, exhibits poor adhesion. Therefore, this sample is of no practical use.

EXAMPLES 7 TO 10

Dermal bandages were prepared in the same manner as in Example 1, except for changing the thickness of the film-like adhesive material as shown in Table 3.

Each of the resulting samples was subjected to the adhesion test and peel test (time of immersion: 10 minutes) in the same manner as in Example 1. Further, a path (5×5 cm) of each sample was applied to the upper arm of 10 panel members. The time till the patch was separated apart was determined, and the feel of application to the skin was evaluated. The results obtained are shown in Table 3 below.

TABLE 3

| | Example No. | | | |
|---|---|---|---|---|
| | 7 | 8 | 9 | 10 |
| Thickness of Film-like Adhesive Material (μm) | 3 | 5 | 200 | 200 |
| Adhesion Time (hr) | 2.5 | 3.1 | 8< | 8< |
| Peel Strength (g/2.5 cm-width) | 20 | 60 | 120 | 120 |
| Adhesion Time (Panel test) (hr) | 0.5 | 1.0 | 8< | 8< |
| Feel to the Skin | Not foreign | Not foreign | Slightly foreign | Slightly foreign |

EXAMPLE 11

| | (part) |
|---|---|
| CVP | 3.4 |
| PVAc (degree of polymerization: about 1,000) | 8.4 |
| Trisodium citrate | 0.2 |
| Methanol | 71.0 |
| Distilled water | 17.0 |

The above components were mixed to form a uniform solution. The resulting solution was flow-cast on a polyethylene terephthalate film and dried in a drier at 80° C. for 15 minutes to obtain a film-like adhesive material having a thickness of 80 μm. The film-like adhesive material had value A of 18. The resulting film-like adhesive material was then hot-pressed onto a 30 μm thick polyethylene film at 100° C. to obtain a dermal bandage.

EXAMPLE 12

| | (part) |
|---|---|
| Methyl vinyl ether-maleic anhydride alternating copolymer | 4.0 |
| PVAc (degree of polymerization: about 1,500) | 6.0 |
| Sodium hydroxide | 0.5 |
| Methanol | 67.5 |
| Ethyl acetate | 22.0 |

The above components were mixed to form a uniform solution. The solution was flow-cast on a 30 μm thick polyethylene film, followed by drying in a drier at 60° C. for 15 minutes to thereby obtain a dermal bandage composed of a 20 μm thick film-like adhesive material integrally bonded with the polyethylene film.

EXAMPLE 13

| | (part) |
|---|---|
| CVP | 3 |
| Methyl vinyl ether-maleic anhydride copolymer | 2 |
| PVAc (degree of polymerization: about 2,000) | 5 |
| Polyethylene glycol (degree of polymerization: about 400) | 10 |
| Methanol | 90 |

The above components were mixed, and the resulting uniform solution was flow-cast on a pater separator, dried at 60° C. and peeled off to obtain a film-like adhesive material having a thickness of 15 μm.

The resulting film-like adhesive material was then hot-pressed on a 30 μm thick PVAc film (degree of polymerization: about 1,500) to obtain a dermal bandage.

EXAMPLE 14

|  | (part) |
|---|---|
| CVP | 4.7 |
| PVAc (degree of polymerization: about 1,000) | 4.7 |
| Methanol | 90.0 |
| Diisopropanolamine | 0.6 |

The above components were mixed to form a uniform solution. The solution was flow-cast on polyethylene-laminated paper which had been subjected to releasing treatment and dried in a drier at 100° C. for 8 minutes to form a film-like adhesive material having a thickness of 40 μm.

The resulting film-like adhesive material was then hot-pressed on a PVAc film (degree of polymerization: about 2,000) having a thickness of 40 μm at 100° C. The composite product thus obtained was sprayed with warm water at 30° C. so as to have a water content of 20%, thereby obtaining a dermal bandage.

Each of the samples of Examples 11 to 14 was evaluated for performances in the same manner as in Examples 7 to 10. The results obtained are shown in Table 4, in which value A of each sample also given.

TABLE 4

|  | Example No. | | | |
|---|---|---|---|---|
|  | 11 | 12 | 13 | 14 |
| Value A | 18 | 23 | 30.3 | 31 |
| Adhesion Time (hr) | 4.3 | 3.7 | 4.4 | 5.6 |
| Peel Strength (g/2.5 cm-width) | 25 | 54 | 110 | 90 |
| Adhesion Time (panel test) (hr) | 9 | 11 | 14 | 12 |
| Feel to the Skin | Not foreign | Not foreign | Not foreign | Not foreign |

As is apparent from Table 4, every sample according to the present invention exhibits strong adhesion of long duration by water absorption. It can also be seen that these samples are very agreeable to the skin with no feel foreign to the skin when actually applied to the human body.

EXAMPLE 15

| Polyacrylic acid | 7.0 parts |
|---|---|
| Polyvinyl acetate (degree of saponification: 20 mol%) | 3.0 parts |
| Zinc oxide | 0.8 part |
| Methanol | 89.2 parts |

The above components were uniformly mixed to form a solution, and Lidocaine was added thereto in an amount of 6% by weight based on the solid content of the solution. The resulting solution was cast on a 60 μm thick film of an ethylene-vinyl acetate copolymer having a vinyl acetate content of 28% by weight, followed by drying in a dryer at 80° C. for 10 minutes to obtain a dermal preparation. The dermal preparation had a Lidocaine content of 720 μg/cm².

COMPARATIVE EXAMPLE 1

| Natural rubber | 10 parts |
|---|---|
| Terpene resin (melting point: 115° C.) | 7 parts |
| Polybutene (molecular weight: 1260) | 3 parts |
| Toluene | 80 parts |

The above components were uniformly mixed to form a solution, and Lidocaine was added thereto in an amount of 6% by weight based on the solid content of the solution. The resulting solution was cast on a silicone-treated paper separator and dried at 120° C. for 4 minutes. A 60 μm thick film of an ethylene-vinyl acetate copolymer having a vinyl acetate content of 28% by weight was then laminated on the cast film to obtain a dermal preparation. The Lidocaine content in the resulting dermal preparation was 720 μg/cm².

Each of the dermal preparations obtained in Example 15 and Comparative Example 1 was dipped in water for 1 second and, immediately thereafter, adhered to the abdomen of rats (6 rats per group) for 3 hours. The Lidocaine content in the dermal preparation after 3 hours' adhesion was measured to obtain the release ratio of Lidocaine. The results obtained are shown in Table below.

TABLE 5

| Example No. | Rat No. | Release Ratio (%) | Average Release Ratio (%) |
|---|---|---|---|
| 15 | 1 | 18.7 |  |
| " | 2 | 19.9 |  |
| " | 3 | 14.8 |  |
| " | 4 | 19.7 | 17.4 |
| " | 5 | 16.3 |  |
| " | 6 | 14.8 |  |
| Comparative Example 1 | 7 | 8.7 |  |
| Comparative Example 1 | 8 | 11.3 |  |
| Comparative Example 1 | 9 | 9.9 |  |
| Comparative Example 1 | 10 | 10.3 | 12.7 |
| Comparative Example 1 | 11 | 19.8 |  |
| Comparative Example 1 | 12 | 16.2 |  |

Then, patches (3 cm×3 cm) were cut out from each of the dermal preparations of Example 15 and Comparative Example 1 and were adhered to the skin of the inside of the upper arm of 10 healthy male panel members. The state of adhesion after 3 hours' adhesion and the pain upon peeling after 3 hours' adhesion were evaluated according to the following ratings:

| Rating | Adhesion | Pain on Peeling |
|---|---|---|
| 1 | Completely adhered | No pain |
| 2 | Partly separated (over area not more ⅓) | Very slight pain |
| 3 | Partly separated (over area not less than ⅓) | Slight pain |

-continued

| Rating | Adhesion | Pain on Peeling |
|---|---|---|
| 4 | Completely separated | Heavy pain |

The results of evaluation are shown in Table 6 below.

TABLE 6

| Panel Member No. | Example 15 | | Comparative Example 1 | |
|---|---|---|---|---|
| | Adhesion | Pain | Adhesion | Pain |
| 1 | 1 | 1 | 1 | 3 |
| 2 | 1 | 1 | 1 | 3 |
| 3 | 3 | 1 | 1 | 1 |
| 4 | 2 | 1 | 2 | 1 |
| 5 | 1 | 1 | 1 | 1 |
| 6 | 3 | 1 | 1 | 1 |
| 7 | 1 | 1 | 1 | 3 |
| 8 | 1 | 1 | 1 | 4 |
| 9 | 1 | 1 | 1 | 3 |
| 10 | 1 | 1 | 1 | 3 |

EXAMPLE 16

| CVP | 4.5 parts |
|---|---|
| PVAc (Degree of polymerization: about 1,000) | 8.5 parts |
| Trisodium citrate | 0.3 part |
| Glycerin | 3.0 parts |
| Methanol | 70.0 parts |
| Purified water | 20.0 parts |

The above components were uniformly mixed to form a solution, and Fluocinonide was added to the solution in an amount of 0.2% by weight based on the solid content of the solution. The resulting solution was cast on a 80 μm thick polyethylene film and dried in a drier at 80° C. for 15 minutes to obtain a dermal preparation containing 8 μg/cm² of Fluocinonide.

COMPARATIVE EXAMPLES 2 AND 3

In a flask were charged 95 parts of 2-ethylhexyl acrylate (EHA), 5 parts of acrylic acid, and 0.3 part of azobisisobutyronitrile (AIBN) in an inert gas atmosphere to initiate polymerization. The polymerization reaction was continued while adding dropwise ethyl acetate and maintaining the reaction temperature at about 60° C. until heat was not generated to obtain a polymer solution (A).

Separately, 65 parts of EHA, 15 parts of 2-methoxyethyl acrylate, 20 parts of vinyl acetate and 0.3 part of benzoyl peroxide were subjected to polymerization in the same manner as described above to obtain a polmer solution (B).

Fluocinonide was added to each of the polymer solutions (A) and (B) so as to have the same content as in the solution of Example 16, and the resulting solution was flow-cast and dried in the same manner as in Example 16 to obtain a dermal preparation.

Discs of 23 mm in diameter were cut out from each of the dermal preparations obtained in Example 16 and Comparative Examples 2 and 3. After the disc of Example 16 was dipped in water for 1 second, each of the dermal preparation obtained in Example 16 and Comparative Example 2 and 3 was adhered to the inside part of the upper arm of 10 healthy male panel members for 6 hours and then peeled off. The score of a blanching test of the skin to which the disc had been applied was observed after 2 hours, 6 hours and 18 hours from the peeling and evaluated according to the following ratings. The results obtained are shown in FIG. 1 as an average of 10 panel members for each disc.

| Score | Blanching test |
|---|---|
| 0 | No white spots were observed |
| 1 | Slight white spots were observed. |
| 2 | Moderate white spots were observed. |
| 3 | Remarkable white spots were observed. |

Figure 1:
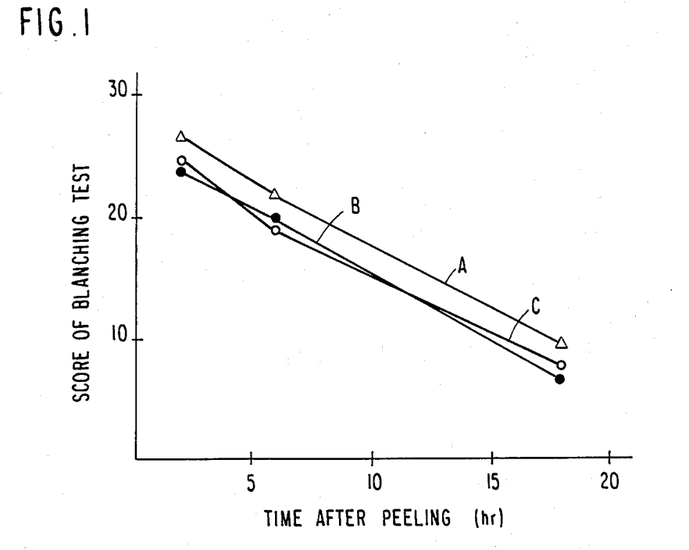
FIGS. 1 and 2 are the graph showing the relationship between the time after peeling and the score of a blanching test (vasoconstriction)

In FIG. 1, Curves A, B and C indicate Example 16 and Comparative Examples 2 and 3, respectively.

EXAMPLE 17

| Methyl vinyl ether-maleic anhydride alternating copolymer | 4.0 parts |
|---|---|
| PVAc (Degree of polymerization: about 1,500) | 6.0 parts |
| Sodium hydroxide | 0.5 parts |
| Methanol | 67.5 parts |
| Ethyl acetate | 22.0 parts |

The above components were uniformly mixed to form a solution, and Prednisolone Valerate was added thereto in an amount of 0.75% by weight based on the solid content of the solution. The solution was flow-cast on a separator
which had been subjected to a release treatment and dried at 100° C. for 5 min, and a 30 μm thick polyethylene film was then laminated on the cast film to obtain a dermal preparation containing 30 μg/cm² of Prednisolone Valerate.

COMPARATIVE EXAMPLES 4 AND 5

Figure 2:
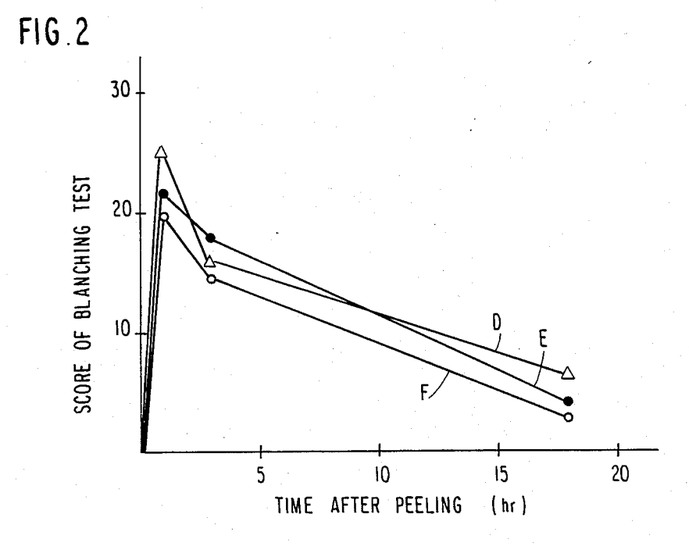

Prednisolone Valerate was added to each of the polymer solutions (A) and (B) as prepared in Comparative Examples 2 and 3, respectively, in an amount of 0.75% by weight based on the solid content of the solution. The resulting solution was flow-cast, dried and laminated in the same manner as in Example 17 to obtain a dermal preparation. The resulting dermal preparation was tested in the same manner as in Example 17 to evaluate its score in the blanching test of the skin after peeling, except that the evaluations were made after 1 hour, 3 hours, and 18 hours from the peeling. The results obtained are shown in FIG. 2, in which Curves D, E and F indicate Example 17 and Comparative Examples 4 and 5, respectively.

EXAMPLE 18

| CVP | 3.0 parts |
|---|---|
| Methyl vinyl ether-maleic anhydride alternating copolymer | 2.0 parts |
| PVAc Degree of polymerization: about 2,000) | 5.0 parts |
| Polyethylene glycol (Degree of polymerization: about 400 | 10.0 parts |
| Methanol | 90.0 parts |

The above components were uniformly mixed to form a solution, and Timolol was added thereto in an amount of 10% by weight based on the solid content of the solution. The resulting solution was cast on a separator which had been subjected to a release treatment and dried at 60° C. for 15 minutes. A 60 μm thick aluminum-deposited polyethylene film was then laminated on the cast film to obtain a dermal preparation having a Timolol content of 400 μg/cm².

COMPARATIVE EXAMPLE 6

100 parts of polyisobutylene (molecular weight: about 1,600,000), 70 parts of polyisobutylene (molecular weight: about 60,000) and 30 parts of an alicyclic saturated hydrocarbon resin (molecular weight: about 700; melting point: 100° C.) were uniformly dissolved in toluene, and Timolol was added thereto in an amount of 10% by weight based on the solid content of the solution. The resulting solution was flow-cast, dried and laminated with an aluminum-deposited polyethylene film in the same manner as in Example 18, except for drying at 120° C. for 5 mins.

Figure 3:
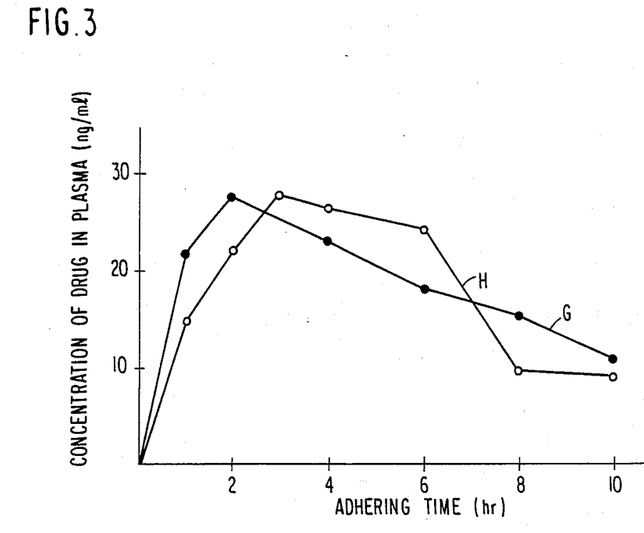
FIGS. 3, 4, 5 and 6 are graphs showing the relationship between the adhering time and the concentration of a drug in plasma.

Each of the dermal preparations obtained in Example 18 and Comparative Example 6 was cut into patches of 50 cm², and each patch was adhered to the shaved abdomen of rats. The blood was taken at a given time interval, and the blood level of Timolol was determined by gas chromatography. The results obtained are shown in FIG. 3, in which Curves G and H indicate Example 18 and Comparative Example 6, respectively.

EXAMPLE 19

| CVP | 4.7 parts |
| PVAc (Degree of polymerization: about 1,000) | 4.7 parts |
| Diisopropanolamine | 0.6 part |
| Glycerin | 8.0 parts |
| Methanol | 90.0 parts |

The above components were uniformly mixed to form a solution, and Clonidine was added thereto in an amount of 5% by weight based on the solid content of the solution. The resulting solution was cast on a separator which had been subjected to a release treatment to a dry thickness of 40 μm, followed by drying at 120° C. for 5 minutes. The cast film was then laminated with a 80 μm thick urethane film to obtain a dermal preparation having a Clonidine content of 200 μg/cm².

COMPARATIVE EXAMPLE 7

85 parts of EHA, 15 parts of N-vinyl-2-pyrrolidone and 0.3 part of AIBN were subjected to polymerization in the same manner as in Comparative Example 2 to obtain a polymer solution (C). To the solution was added Clonidine in an amount of 5% by weight based on the solid content of the solution, and the resulting solution was flow-cast, dried, and laminated with a urethane film in the same manner as in Example 19 to obtain a dermal preparation having a Clonidine content of 200 μg/cm².

Figure 4:
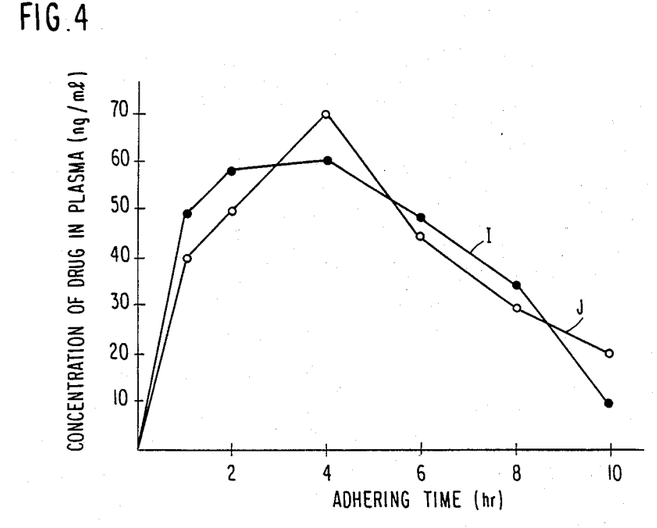

Each of the dermal preparations of Example 19 and Comparative Example 7 was cut into patches having a size of 10 cm², and each patch was adhered to the shaved abdomen of rats. The blood was taken at a given time interval, and the blood level of Clonidine was determined by gas chromatography. The results obtained are shown in FIG. 4, in which Curves I and J indicate Example 19 and Comparative Example 7, respectively.

EXAMPLE 20

| CVP | 4.0 parts |
| PVAc (Degree of polymerization: about 1,000) | 6.0 parts |
| Trisodium citrate | 0.7 part |
| Propylene glycol | 6.0 parts |
| Methanol | 100.0 parts |

The above components were uniformly mixed to form a solution, and Isosorbide Dinitrate was added thereto in an amount of 15% by weight based on the solid content of the solution. The resulting solution was cast on a separator which had been subjected to a release treatment to a dry thickness of 40 μm, followed by drying at 100° C. for 5 minutes. A 80 μm thick polyethylene film was then laminated on the cast film to obtain a dermal preparation having an Isosorbide Dinitrate content of 600 μg/cm².

COMPARATIVE EXAMPLE 8

To the polymer solution (A) as prepared in Comparative Example 2 was added Isosorbide Dinitrate in an amount of 15% by weight based on the solid content of the solution. The resulting solution was flow-cast, dried, and laminated with a polyethylene film in the same manner as in Example 20 to obtain a dermal preparation having a content of Isosorbide Dinitrate of 600 μg/cm².

Figure 5:
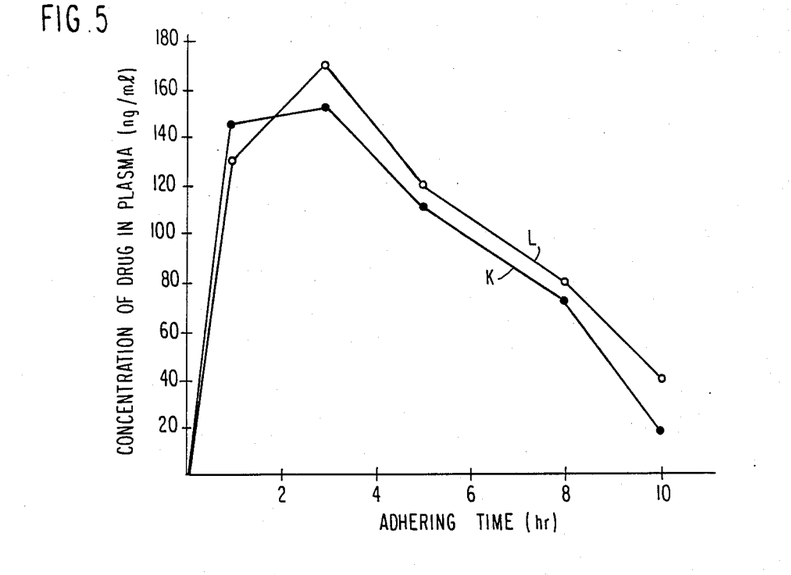

Each of the dermal preparations prepared in Example 20 and Comparative Example 8 was cut into patches having a size of 65 cm² and adhered to the shaved back of rabbits. The dermal preparation prepared in Example 20 was adhered to the shave back of rabbits after spraying water onto the shaved back for moisturization. The blood was taken at a given time interval, and the blood level of Isosorbide Dinitrate was determined by gas chromatography. The results obtained are shown in FIG. 5, in which Curves K and L indicate Example 20 and Comparative Example 8, respectively.

EXAMPLE 21

| CVP | 3.0 parts |
| Polyacrylic acid (Degree of polymerization: about 5,000) | 2.0 parts |
| PVAc (Degree of polymerization: about 1,500) | 5.0 parts |
| Trisodium citrate | 0.7 part |
| Methanol | 87.0 parts |

The above components were uniformly mixed to form a solution, and Diclofenac was added thereto in an amount of 5% by weight based on the solid content of the solution. The resulting solution was cast on a separator which had been subjected to a release treatment and dried at 120° C. for 5 minutes to obtain a dermal preparation having a Diclofenac content of 500 μg/cm².

COMPARATIVE EXAMPLE 9

Diclofenac was added to the polymer solution (B) as prepared in Comparative Example 3 in an amount of 5% by weight based on the solid content of the solution. The resulting solution was flow-cast and dried in the same manner as in Example 21 to obtain a dermal preparation having a Diclofenac content of 500 μg/cm².

Figure 6:
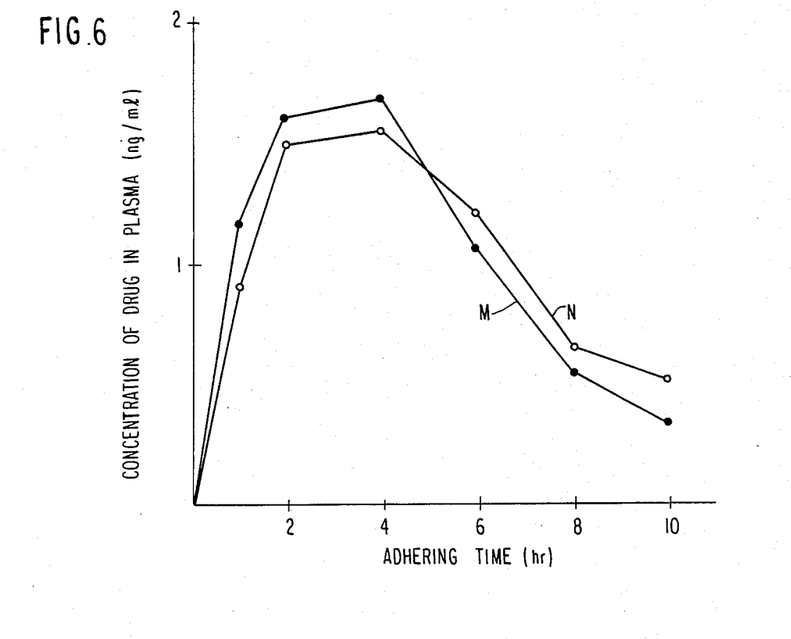

Each of the dermal preparations obtained in Example 21 and Comparative Example 9 was cut into patches having a size of 13.5 cm² and adhered to the shaved abdomen of rats. The blood was taken at a given time interval, and the blood level of Diclofenac was determined by gas chromatography. The patch of Example was dipped in water for 1 second before adhesion. The results obtained are shown in FIG. 6, in which Curves M and N indicate Example 21 and Comparative Example 9, respectively.

While the invention has been described in detail and with reference to specific examples thereof, it will be apparent to one skilled in the art that various changes and modifications can be made therein without departing from the spirit and scope thereof.

What is claimed is:

1. A dermal bandage comprising a film-like adhesive material comprising:
   (a) vinyl acetate polymer and
   (b) at least one of polycarboxylic acid and polycarboxylic acid anhydride; wherein if a polycarboxylic acid is used, then said film-like adhesive material comprises 20% by weight or more of a —COOH group, and if a polycarboxylic acid anhydride is used, then said film-like adhesive material comprises 16% by weight or more of a —CO—O—CO—group; and wherein a ratio of the polycarboxylic acid and/or polycarboxylic acid anhydride to the vinyl acetate polymer is in such a range that a value defined by formula:

$$\frac{\text{Weight of —COOH in Film-like Adhesive Material} + \frac{5}{4} \text{Weight of —CO—O—CO— in Film-like Adhesive Material}}{\text{(Weight of Polycarboxylic Acid + Weight of Vinyl Acetate Polymer) in Film-like Adhesive Material}} \times 100$$

2. A dermal bandage as in claim 1, wherein the film-like adhesive material contains at least one of polycarboxylic acid and polycarboxylic acid anhydride in an amount of 20 to 75% by weight based on the weight of the film-like adhesive material.

3. A dermal bandage as in claim 1, wherein said polycarboxylic acid and polycarboxylic acid anhydride are selected from the group consisting of an acrylic acid homopolymer, an acrylic acid copolymer, a methacrylic acid hompolymer, a methacrylic acid copolymer, a maleic anhydride homopolymer, and a maleic anhydride copolymer.

4. A dermal bandage as in claim 1, wherein said vinyl acetate polymer is selected from the group consisting of vinyl acetate homopolymer, a vinyl acetate copolymer with a vinyl monomer, and a partially saponified vinyl acetate homopolymer.

5. A dermal bandage as in claim 1, wherein said vinyl acetate polymer has a viscosity average molecular weight of 86,000–215,000.

6. A dermal bandage as in claim 1, wherein said adhesive film has a thickness of from 5 to 500 μm.

7. A dermal bandage as in claim 1, wherein said film-like adhesive material further contains a plasticizer.

8. A dermal bandage as in claim 7, wherein said plasticizer is polyethylene glycol.

9. A dermal bandage as in claim 1, wherein said film-like adhesive material further contains up to 50% by weight of water.

10. A dermal bandage as in claim 1, wherein said film-like adhesive material is laminated on a soft backing member.

11. A dermal bandage as in claim 10, wherein said backing member has a thickness of from 5 to 1,000 μm and a total thickness of the film-like adhesive material and the backing member is from 30 to 1,500 μm.

12. A dermal preparation comprising a film-like adhesive material comprising a mixture of:
    (a) vinyl acetate polymer,
    (b) at least one of polycarboxylic acid and polycarboxylic acid anhydride, and
    (c) a drum incorporated therein; wherein if polycarboxylic acid are used, then said film-like adhesive material comprises 20% by weight or more of a —COOH group, and if polycarboxylic acid anhydride are used, then said film-like adhesive material comprises 16% by weight or more of a —CO—O—CO—group; and wherein a ratio of the polycarboxylic acids and/or polycarboxylic acid anhydride to the vinyl acetate polymer is in such a range that a value defined by:

$$\frac{\text{Weight of —COOH in Film-like Adhesive Material} + \frac{5}{4} \text{Weight of —CO—O—CO— in Film-like Adhesive Material}}{\text{(Weight of Polycarboxylic Acid + Weight of Vinyl Acetate Polymer) in Film-like Adhesive Material}} \times 100$$

is from 15 to 55.

13. A dermal preparation as in claim 12, wherein the drug is solid or liquid at room temperature, which can be dissolved or dispersed in the film-like adhesive material.

14. A dermal preparation as in claim 12, wherein the amount of the drug is 0.001 to 30% by weight based on the weight of the film-like adhesive material.

15. A dermal preparation as in claim 12, wherein the film-like adhesive material contains at least one of polycarboxylic acid and polycarboxylic acid anhydride in an amount of 20 to 75% by weight based on the weight of the film-like adhesive material.

16. A dermal preparation as in claim 12, wherein said polycarboxylic acid and polycarboxylic acid anhydride are selected from the group consisting of an acrylic acid homopolymer, an acrylic acid copolymer, a methacrylic acid homopolymer, a methacrylic acid copolymer, a maleic anhydride homopolymer, and a maleic anhydride copolymer.

17. A dermal preparation as in claim 12, wherein said vinyl acetate polymer is selected from the group consisting of vinyl acetate homopolymer, a vinyl acetate copolymer with a vinyl monomer, and a partially saponified vinyl acetate homopolymer.

18. A dermal preparation as in claim 12, wherein said vinyl acetate polymer has a viscosity average molecular weight of 86,000–215,000.

19. A dermal preparation as in claim 12, wherein said adhesive film has a thickness of from 5 to 500 μm.

20. A dermal preparation as in claim 12, wherein said film-like adhesive material further contains a plasticizer.

21. A dermal preparation as in claim 20, wherein said plasticizer is polyethylene glycol.

22. A dermal preparation as in claim 12, wherein said film-like adhesive material further contains up to 50% by weight of water.

23. A dermal preparation as in claim 12, wherein said film-like adhesive material is laminated on a soft backing member.

24. A dermal preparation as in claim 23, wherein said backing member has a thickness of from 5 to 1,000 μm and a total thickness of the film-like adhesive material and the backing member is from 30 to 1,500 μm.

* * * * *